United States Patent [19]

Franetzki et al.

[11] 4,191,181
[45] Mar. 4, 1980

[54] APPARATUS FOR INFUSION OF LIQUIDS

[75] Inventors: Manfred Franetzki, Uttenreuth; Karl Prestele, Erlangen; Helmut Funke, Möhrendorf, all of Fed. Rep. of Germany

[73] Assignee: Siemens Aktiengesellschaft, Berlin & Munich, Fed. Rep. of Germany

[21] Appl. No.: 845,711

[22] Filed: Oct. 26, 1977

[30] Foreign Application Priority Data

Nov. 15, 1976 [DE] Fed. Rep. of Germany ....... 2652026

[51] Int. Cl.² ........................... A61J 7/00; A61M 5/00
[52] U.S. Cl. ............................ 128/213 R; 128/214 F; 128/DIG. 12
[58] Field of Search ............... 128/214 F, 213, 214 E, 128/215, 260; 222/386.5, 95, 96, 105, 107

[56] References Cited

U.S. PATENT DOCUMENTS 3,496,878  2/1970  Hargest et al. .................... 128/214 F
3,731,681  5/1973  Blackshear et al. ............. 128/214 F Primary Examiner—Robert W. Michell
Assistant Examiner—C. W. Shedd
Attorney, Agent, or Firm—Hill, Van Santen, Steadman, Chiara & Simpson

[57] ABSTRACT

An apparatus for infusion of liquids into human or animal bodies which comprises a liquid reservoir having a reduced-pressure generating means associated therewith and an active delivery-dosing means, such as a roller pump, operationally coupled with the reservoir and with an outflow catheter having outflow opening within the body being infused. The reduced-pressure generating means, such as a volatile fluid, for example, a halogenated hydrocarbon, maintains a pressure at the point of connection between the reservoir and the active delivery-dosing means at a reference value which is lower than the pressure prevailing at the outflow opening of the outflow catheter.

20 Claims, 3 Drawing Figures

APPARATUS FOR INFUSION OF LIQUIDS

BACKGROUND OF THE INVENTION

1. Field of the Invention

The invention relates to an apparatus for infusion of liquids and somewhat more particularly to a fail-safe apparatus for infusion of liquid medications into human or animal bodies.

2. Prior Art

In the treatment of patients, whether human or animal, with liquid medications, the medications must be delivered from a reservoir through an outflow catheter in such a manner that the amount of liquid infused per unit time can be accurately dosed and controlled. This is particularly acute in instances where, for example, in the treatment of diabetes, insulin must be continuously infused at different controllable rates because the insulin demand of a diabetic may be subject to considerable fluctuations during the course of any one day. Such fluctuations may be caused, for example, because of a variable frequency of meal times. For an insulin concentration of, for example, 500 IE/ml in the infusion liquid, catheter flow rates in the order of microliters per hour (for example, $10^{-6}$ 1/hr), are necessary. A daily dose for a given patient may correspond to about 1 to 2 drops of infusion liquid.

Presently known devices for infusion of liquids into human or animal bodies generally comprise a reservoir for the infusion liquid and a controllable delivery-dosing means coupled thereto for delivering the liquid from the reservoir to the outflow opening of an outflow catheter. Such devices may be implanted in the body of a patient or may be worn outside the body. Typically, the prior art devices utilize a combination of an excess pressure and a flow resistance as the delivery-dosing means. In such devices, a constant flow, controllable by valves, is produced by the action of the excess pressure on the volume of liquid through-flow in the resistance, for example, in the form of a capillary. By connecting two flow resistances in parallel, some of these devices attain a constant basal rate with a periodically activatable peak rate. However, the use of valves in association with an excess pressure producing means, particularly when applied to human bodies, is dangerous or at least disadvantageous because if there is a failure of the valves, the flow of medication into the body is not stopped. For example, in the treatment of diabetes, an overdose of insulin can cause serious damage to a patient. Accordingly, in order to insure optimum patient safety, there is a need for an infusion device capable of delivering only a particular volume of liquid from a reservoir to the outflow catheter despite any mechanical failure or malfunction.

SUMMARY OF THE INVENTION

The invention provides an infusion device which is capable of accurately controlling, with absolute certainty and despite any mechanical malfunctions, the outflow of infusion liquids from a reservoir into a body.

In accordance with the principles of the invention, a liquid reservoir is operationally associated with a reduced-pressure generating means which maintains a pressure at the connection between the reservoir and the delivery-dosing means at a value below that prevailing at the outflow opening of an outflow catheter.

The device of the invention thus solves the above-referenced prior art problem in an extremely efficient and simple manner. On the one hand, a controllable or pre-programmable delivery-dosing means, such as an active pump, i.e., a roller pump, is utilized so as to completely dispense with active valves or flow resistors and on the other hand, the patient is guaranteed absolute safety in the event of mechanical failure since no infusion liquid can be discharged under the effect of reduced pressure.

In a preferred embodiment of the invention, the reduced pressure on the infusion liquid is produced by the vapor pressure of a volatile fluid, such as a halogenated hydrocarbon, for example, Frigen R 113, (a registered trademark for commercially available 1,1,2-trichloro-1,2,2-trifluoroethane). Because of their special vapor pressure curves, volatile liquids such as halogenated hydrocarbons are especially useful in the practice of the invention since their vapor pressure at body temperatures naturally corresponds to the required reference pressure value or to a preselected reference pressure value which may be just below expected external air pressure and which may be attained by mixing specific volatile fluids of this type. Any change in air pressure, such as attributable to different altitudes, may be taken into consideration when preparing a suitable volatile fluid mixture. Similarly, changes in vapor pressure of the vaporizable fluid attributable to possible increases in body temperatures (such as during a fever) may also be taken into consideration in selecting a suitable volatile fluid.

In one embodiment of the invention, the vaporizable fluid and the infusion liquid are arranged in separate chambers which are connected by a pressure-transmissive medium, such as a flexible membrane. In another embodiment of the invention, a volatile fluid is selected so as to be immiscible with the infusion liquid and both fluids are arranged within a common chamber and a wick-like flexible tube which exhibits better wetting properties for the infusion liquid relative to the volatile fluid is provided within such a common chamber and in communication with a delivery-dosing means. In yet another embodiment of the invention, the entire housing of the infusion device is encapsulated in a gas impermeable manner and provided with a gas having a reduced pressure at body temperatures. In this embodiment, the space within the housing left unoccupied by the components of the device act as a buffer volume on the infusion liquid which is located within the buffer volume in a flexible bag and on which the gas exerts a force corresponding to the reduced pressure thereof.

DESCRIPTION OF THE PREFERRED EMBODIMENTS

The invention provides a device for infusion of liquids into human or animal bodies in a fail-safe manner whereby a select reduced-pressure generating means acts on an infusion liquid reservoir so as to force such infusion liquid into a delivery-dosing means.

In accordance with the principles of the invention, the pressure utilized to force an infusion liquid from a reservoir (which is isolated from the body being treated with the infusion liquid thereof into a delivery-dosing means generated by a volatile fluid or a mixture of fluids which exhibit a vapor pressure which is at a reduced value relative to the ambient pressure or pressure within the body. A preferred class of such volatile fluids comprises halogenated hydrocarbons as exemplified by Frigen R 113 (a registered trademark for commercially available 1,1,2-trichloro-1,2,2-trifluoroethane). Volatile fluids which exhibit a reduced or sub-atmospheric vapor pressure at body temperatures have special vapor pressure curves which yield vapor pressure at body temperatures that naturally correspond to the required reduced pressure (i.e., below atmospheric pressure and/or below the pressure prevalent within a human or animal body) for safely forcing an infusion liquid into a patient via a delivery-dosing means. Changes in air pressure and/or body temperature may be compensated for by mixing specific volatile fluids so as to attain a required vapor pressure at the changed condition.

Figure 1:
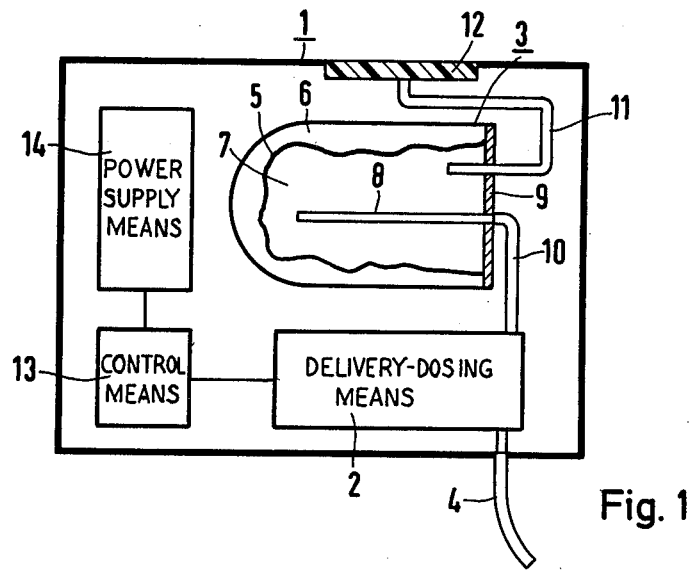
FIG. 1 is an elevated, somewhat schematic view of one infusion device constructed in accordance with the principles of the invention wherein the infusion liquid and the volatile fluid are located in separate chambers within a reservoir means.

A first exemplary embodiment of the invention is illustrated at FIG. 1 and includes a housing 1 which comprises a gas impermeable capsule or body composed of a material compatible with tissue so as to be implantable within a human or animal body. A preferred embodiment of such tissue-compatible material is titanium. A delivery-dosing means 2, such as an active pump, is operationally positioned within the interior housing 1. A preferred embodiment of such an active pump is a roller pump. An infusion liquid reservoir means 3 is also operationally arranged within the housing 1. A tube 10 interconnects the reservoir means 3 with the delivery-dosing means 2 and one end of an outflow catheter 4 is coupled to the output end of the delivery-dosing means 2. The reservoir means 3 includes an inner chamber 7 and an outer chamber 6 separated from one another by a flexible partition or membrane 5. The outer chamber 6 is provided with a select reduced or sub-atmospheric pressure generating means, preferably a fluid having a suitable vapor pressure curve, such as the earlier noted Frigen R 113. Halogenated hydrocarbons of this type have a vapor pressure at body temperature which is just below the external normal atmosphere or air pressure. By mixing specific volatile fluids of this type, one can readily attain a reduced-pressure (vapor pressure) value which is just below the expected ambient pressure. The volatile fluid applies a pressure on the inner chamber 7 through partition 5 which corresponds to the vapor pressure of the volatile fluid within chamber 6. A select infusion liquid is positioned within the interior chamber 7. A suction-like connecting piece comprised of rod 8 having at least one inner lumen composed of a porous material having fine pores throughout the lumen is positioned within the chamber 7 to function as an outlet for the infusion liquid therein. The entire reservoir means 3 is preferably formed from a cylindrical bag-like container having the open end thereof sealed with a relatively rigid cover 9 which is provided with a suitable number of outlet openings for ingress and egress of infusion liquid from the reservoir means. The partition or membrane 5 between chambers 6 and 7 is preferably formed of a flexible, durable, synthetic plastic material which is compatible with the infusion liquid and also with the volatile pressure-generating fluid. The vapor pressure of the volatile fluid within chamber 7 acting through partition 5 produces a temporally constant pressure, i.e., a defined reference pressure value, on the infusion liquid independent of the volume within the reservoir. The delivery-dosing means 2, preferably an active roller pump, delivers the infusion liquid to the outflow catheter against this reference pressure. The infusion liquid is drawn through the lumen within rod 8 through a first outlet opening in cover 9 and is discharged into a delivery tube 10 which provides a flow path through the delivery-dosing means 2 and to an outlet opening of an outflow catheter 4. The inner chamber 7 of reservoir 3 is also provided with a connecting tube 11, which extends outwardly from the chamber 7 through another opening in cover 9 and provides fluid communication with a refill valve 12. The refill valve 12 is comprised of an elastic self-sealing plastic material so that when a device has been implemented into a body, refilling of infusion liquid can be effected percutaneously via a syringe. A power supply means 14, such as a battery, and a control means 13 are positioned within housing 1 and operationally coupled to the delivery-dosing means 2.

Figure 2:
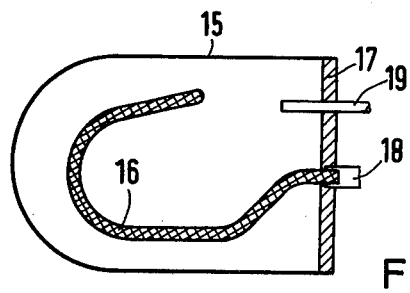
FIG. 2 is a somewhat similar view of another embodiment of a reservoir means constructed in accordance with the principles of the invention wherein the infusion liquid and the volatile fluid are located in a common chamber.

In FIG. 2, only an embodiment of a reservoir means has been shown for the sake of simplicity and it will be understood that such reservoir means is positioned within a suitable housing having an operational and controllable delivery-dosing means coupled therewith as explained earlier. In this embodiment, the reservoir means 15 is provided with a multi-component mixture of infusion liquid, volatile fluid and vapor in equilibrium therewith. The vapor pressure of the infusion liquid is negligible in relation to that of the volatile fluid. However, this embodiment of the reservoir 15 assumes that the infusion liquid and the voltaile fluid are immiscible with one another, which is the case, for example, with the earlier noted Frigen R 113 in an aqueous infusion solution or liquid. In this embodiment, the infusion liquid outlet comprises a flexible absorbent wick-like member 16 which extends from the interior of the reservoir through one of the outlet openings of cover 17 and is coupled to an end of a delivery tube 18. The reservoir means can be refilled through a connecting tube 19. The wick-like member 16 is composed of a material which is compatible with the infusion liquid and with the volatile fluid and which exhibits distinctly superior wetting properties for the infusion liquid as contrasted to that for the volatile fluid. In one exemplary embodiment, the work member 16 may be composed of tightly packed glass-like (i.e., glass) fibers. The capillary forces within the fine wick channels so-produced prevent vapor from penetrating into the wick member 16 and insure that only infusion liquid is delivered to the patient via an active delivery-dosing means.

Figure 3:
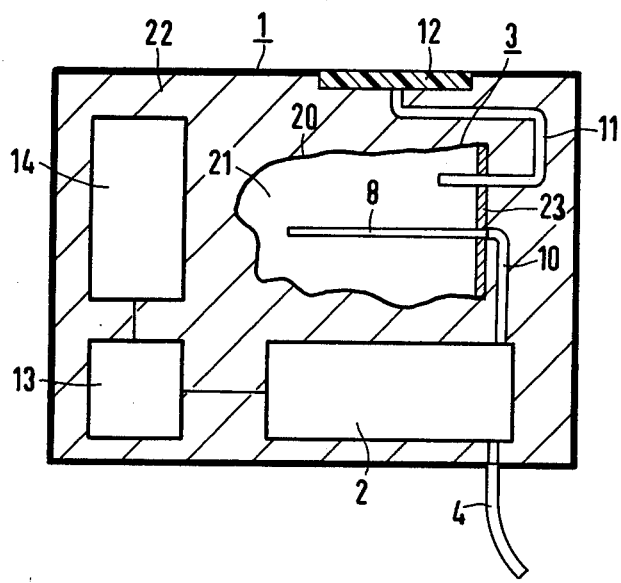
FIG. 3 is a view somewhat similar to that of FIG. 1 of yet another embodiment of an infusion device constructed in accordance with the principles of the invention wherein the volatile fluid is located within the housing surrounding the infusion liquid-containing chamber.

In the embodiment illustrated at FIG. 3, the infusion device comprises a gas impermeable housing 1, which includes therein a power supply means 14, a control means 13, an infusion liquid reservoir means 20, an outflow catheter 4, a delivery tube 10 and connecting or refilling tube 11, as well as a refill valve 12, all operationally coupled as explained in conjunction with FIG.

1. The inner space 22 within housing 1 which is not occupied by the various components of the infusion device is utilized as a buffer volume for a gas functioning as the reduced-pressure generating means. Thus, in the embodiment shown, the reservoir means 20, in contrast to the embodiment discussed at FIG. 1, merely consists of a single chamber or volume 21 within a flexible membrane having a porous suction rod 8 within an inner lumen projecting therefrom. The membrane forming the bag is sealed by substantially rigid cover 23 having appropriate openings therethrough. To generate a desired reduced pressure, a buffer gas having a corresponding reduced pressure value is introduced within space 22 during encapsulation of housing 1. The gas pressure acts as an external pressure force on membrane 20 and thus maintains the infusion liquid within membrane 20 at a corresponding reference pressure value.

In the embodiment illustrated at FIG. 3, the membrane 20 is flexible. However, a suitable infusion liquid reservoir means may also be formed of a low rigidity bellows-like membrane so that gas pressure on the outside of such membrane is adapted to the elastic properties of the bellows-like membrane in such a way that the reference pressure value is adjusted within the bellows-like membrane.

An advantage of the embodiment illustrated at FIG. 3 is that only the constituent materials of the durable membrane 20 and suction rod 8 have to be compatible with the infusion liquid. Thus, the compatibility of these materials with the volatile fluid is no longer necessary. In this embodiment, as the reservoir is progressively emptied by the delivery of infusion liquid to the outflow catheter, the membrane 20 is compressed and the volume 21 thus reduced, which is then occupied by the buffer gas. In this manner, the pressure in the buffer volume 22 is reduced commensurately with the increase of the buffer volume. Accordingly, the overall buffer volume 22 is dimensioned sufficiently large so that the function of the active delivery-dosing means is not materially impaired by the reduction of the reference pressure value in chamber 21 of the reservoir means 20.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention as claimed.

We claim as our invention:

1. A device for infusion of liquids into human or animal bodies comprising:
   a reservoir means for infusion liquids isolated from a body being treated with such infusion liquid;
   a delivery-dosing means operationally coupled to said reservoir means and to an outflow catheter adapted to be connected to a body being treated with the infusion liquid; and
   a reduced-pressure generating means operationally engaged with said reservoir means which maintains a defined reference pressure value at the interconnection between said reservoir means and said delivery-dosing means which is lower than the pressure prevailing at an outflow opening of said outflow catheter.

2. A device as defined in claim 1 wherein said reference pressure value is produced by the vapor pressure of a volatile fluid.

3. A device as defined in claim 2 wherein said volatile fluid comprises a halogenated hydrocarbon fluid having a vapor pressure at body temperatures naturally corresponding to said reference pressure value.

4. A device as defined in claim 3 wherein said halogenated hydrocarbon fluid comprises a mixture of different halogenated hydrocarbons so that such mixture of halogenated hydrocarbons has a vapor pressure corresponding to a preselected value below an expected external air pressure.

5. A device as defined in claim 1 wherein said reservoir means includes a membrane for confining infusion liquid and a substantially rigid cover sealing such membrane and having outlet openings therein for providing ingress and egress of infusion liquid from said reservoir means.

6. A device as defined in claim 5 wherein said membrane is composed of a durable and flexible material.

7. A device as defined in claim 5 wherein said reservoir means contains a mixture comprised of infusion liquid, volatile fluid and vapor, said infusion liquid and volatile fluid being immiscible with one another.

8. A device as defined in claim 5 wherein said reservoir means includes at least an inner and an outer chamber separated from one another via a flexible membrane, said outer chamber being filled with a volatile liquid and said inner chamber being filled with an infusion liquid so that the vapor pressure of said volatile fluid acts as an external pressure force on the infusion liquid through the flexible membrane.

9. A device as defined in claim 8 wherein said flexible membrane is composed of a material which is compatible with the infusion liquid and with the volatile fluid.

10. A device as defined in claim 1 wherein said reservoir means comprises a space surrounded by a membrane located within a buffer volume filled with a gas producing said reference pressure value, said buffer volume being dimensioned sufficiently large so that any reduction of said space within the membrane does not produce any substantial decrease in said reference pressure value.

11. A device as defined in claim 10 wherein said reservoir means is located within a gas impermeable housing having a power supply means, a control means, a delivery-dosing means, means operationally coupling said means with one another and with a patient and said buffer means is defined by the inner space within said housing not occupied by said means.

12. A device as defined in claim 10 wherein said membrane comprises a flexible bellows-like membrane having a relatively low degree of rigidity.

13. A device as defined in claim 1 wherein said reservoir means is operationally coupled to said delivery-dosing means via a fluid passage means composed of a material at least compatible with the infusion liquid.

14. A device as defined in claim 13 wherein said fluid-passage means comprises a porous suction rod having at least one inner pore therein extending from the interior of said reservoir means through an outlet opening of said reservoir means to said delivery-dosing means.

15. A device as defined in claim 13 wherein said fluid-passage means comprises a wick member which exhibits better wetting properties for infusion liquid than for volatile fluid.

16. A device as defined in claim 15 wherein said wick member is composed of individual tightly packed glass-like fibers.

17. A device as defined in claim 15 wherein said wick member is composed of a material compatible with the volatile fluid.

18. A device as defined in claim 1 wherein said reservoir means includes a refill valve means to enable said reservoir means to be refilled from the exterior thereof.

19. A device as defined in claim 18 wherein said refill valve means is comprised of an elastic self-sealing material.

20. A device as defined in claim 1 wherein said reservoir means and said delivery-dosing means are positioned within a gas impermeable housing composed of a body-compatible material.

* * * * *